(12) United States Patent
Metcalfe et al.

(10) Patent No.: US 9,421,105 B2
(45) Date of Patent: Aug. 23, 2016

(54) HUMERAL COMPONENT OF A SHOULDER PROSTHESIS

(71) Applicant: Arthrex, Inc., Naples, FL (US)

(72) Inventors: Nick J. T. Metcalfe, Munich (DE); Gerlinde Michel, Munich (DE); Gregory A. Guederian, Naples, FL (US); Peter Habermayer, Heidelberg (DE); Anthony A. Romeo, Willowbrook, IL (US); Stefan Krupp, Munich (DE); Steven L. Vandermeulen, Ft. Myers, FL (US); Kevin J. Gallen, Naples, FL (US)

(73) Assignee: Arthrex, Inc., Naples, FL (US)

( * ) Notice: Subject to any disclaimer, the term of this patent is extended or adjusted under 35 U.S.C. 154(b) by 337 days.

(21) Appl. No.: 14/196,674

(22) Filed: Mar. 4, 2014

(65) Prior Publication Data
US 2014/0188232 A1      Jul. 3, 2014

Related U.S. Application Data

(62) Division of application No. 13/346,901, filed on Jan. 10, 2012, now Pat. No. 8,663,333.

(60) Provisional application No. 61/431,606, filed on Jan. 11, 2011.

(51) Int. Cl.
*A61F 2/40*     (2006.01)
*A61F 2/30*     (2006.01)

(52) U.S. Cl.
CPC .............. *A61F 2/4014* (2013.01); *A61F 2/4059* (2013.01); *A61F 2002/3038* (2013.01); *A61F 2002/3054* (2013.01); *A61F 2002/30387* (2013.01); *A61F 2002/30405* (2013.01); *A61F 2002/30433* (2013.01); *A61F 2002/30604* (2013.01); *A61F 2002/4018* (2013.01); *A61F 2002/4022* (2013.01); *A61F 2002/4051* (2013.01); *A61F 2002/4074* (2013.01)

(58) Field of Classification Search
CPC .................... A61F 2/40; A61F 2002/30538
USPC ............................................ 623/19.11, 19.14
See application file for complete search history.

(56) References Cited

U.S. PATENT DOCUMENTS

| 5,645,607 | A | 7/1997 | Hickey |
| 6,749,637 | B1 | 6/2004 | Baehler |
| 2006/0200249 | A1 | 9/2006 | Beguin et al. |

FOREIGN PATENT DOCUMENTS

| EP | 0 712 617 A1 | 5/1996 |
| FR | 2 773 469 A1 | 7/1999 |
| WO | WO 01/22905 A1 | 4/2001 |

*Primary Examiner* — Christopher D Prone
*Assistant Examiner* — Christine Nelson
(74) *Attorney, Agent, or Firm* — Blank Rome LLP

(57) ABSTRACT

A humeral component of a shoulder prosthesis encloses a stem module which has a shank and an upper shank portion with a stem support surface. A joint adapter is adapted to hold either a liner or a spherical cap. The joint adapter has an adapter support surface which interfaces with the stem support surface. Further, the stem support surface and the adapter support surface have corresponding radial arc shaped sections which allow positioning of the joint adapter against the stem module at different inclination angles. For fastening the joint adapter to the stem module, a bolt or screw is provided.

12 Claims, 19 Drawing Sheets

Fig. 19
Fig. 20
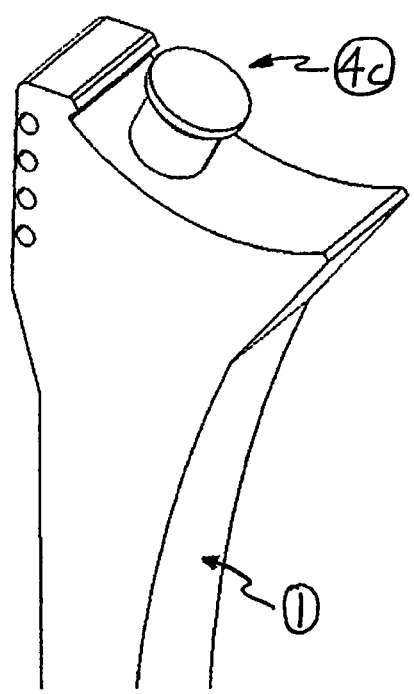
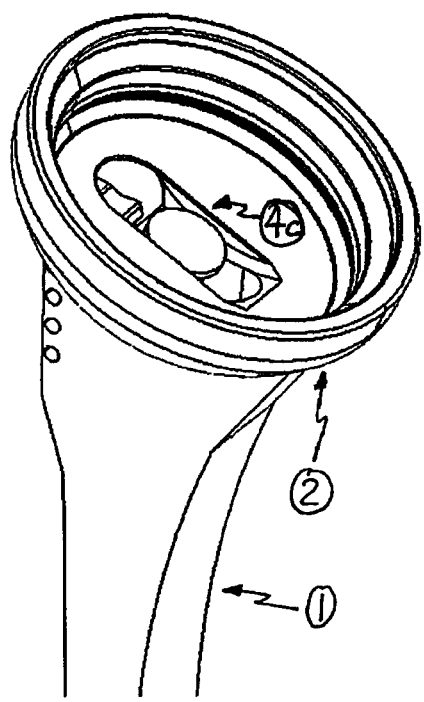

Detail 1

1

HUMERAL COMPONENT OF A SHOULDER PROSTHESIS

CROSS-REFERENCE TO RELATED APPLICATIONS

This is a divisional of U.S. patent application Ser. No. 13/346,901, filed on Jan. 10, 2012, now U.S. Pat. No. 8,663,333, which claims the benefit of U.S. Provisional Application No. 61/431,606, filed Jan. 11, 2011, the entire disclosure of which is incorporated by reference herein.

FIELD OF THE INVENTION

The present invention relates to a modular shoulder arthroplasty system for surgical reconstitution of the shoulder and, in particular, to prosthetic replacement of the humerus.

BACKGROUND OF THE INVENTION

The shoulder joint is a ball-and-socket joint which has an exceptional range of motion. Shoulder instability and other maladies of the shoulder joint, such as arthrosis or fracture, may require a replacement of the joint.

A shoulder joint prosthesis which includes the replacement of the convex head of the humerus is disclosed in U.S. Pat. No. 7,819,923. It reflects the orientation and the center of rotation of actual joints. In the case of a worn or damaged rotator cuff or too much bone loss, such a prosthesis would not recover the range of motion. In such case, a reverse shoulder prosthesis may be preferable. An example of such a prosthesis is disclosed in U.S. Patent Application Publication No. 2009/0210065, where the prosthesis includes a humeral component with a stem and a cup attached to the stem. The glenoid component supports a convex head which articulates with the cup of the humeral component.

To obtain a maximum range of motion, the prosthesis must be adapted to the individual case. Specifically, the position of the cup of the humeral component with respect to the stem is critical. The cup disclosed in U.S. Patent Application Publication No. 2009/0210065 may be pivoted about the axis of the stem.

Instability and other maladies of human joints, such as arthrosis or fracture, can be sufficiently acute that prosthetic replacement of compromised joint features may be indicated. For example, in shoulder reconstruction, the humeral head may be replaced by first resecting the humeral head from the humerus and then installing a humeral prosthetic at the resection.

SUMMARY OF THE INVENTION

The problem to be solved by the invention is to provide the humeral component of a modular shoulder arthroplasty system which may be used either as a joint replacement or as a reverse prosthesis. Another problem to be solved is to further improve adaption of the prosthesis to optimize the range of motion. An improved modular shoulder arthroplasty system that is designed to address any or all of osteoarthritis, trauma and cuff tear arthropathy is also needed.

In an embodiment, the humeral component of a shoulder prosthesis includes a stem module (1) and a joint adapter (2, 6, 7). The stem module has a shank (1a, 1b) with an upper shank portion (1b). The upper shank portion bears a stem support surface (1c) to support a joint adapter. The joint adapter (2, 6, 7) is adapted to hold either a liner (3) in case of a reverse prosthesis or a spherical cap (8) for the use as a joint replacement. This allows to use the stem module either for a reverse prosthesis or a joint replacement. Further, the joint adapter (2, 6, 7) has an adapter support surface (2c) which interfaces with the stem support surface (1c). Research has shown that the inclination angle of the joint and therefore of the joint adapter has the largest effect on adduction of the shoulder. Accordingly, the stem module (1) and the joint adapter (2, 6, 7) are adjustable in the inclination angle. For this purpose, the stem support surface (1c) and the adapter support surface (2d) have corresponding approximately radial arc shaped sections which allow positioning of the joint adapter (2, 6, 7) against the stem module at different inclination angles between the longitudinal axis of the stem module (1) and the center axis of the joint adapter (2, 6, 7). Preferably the stem support surface (1c) and the adapter support surface (2d) have corresponding essentially radial arc shaped sections which may comprise segments of a cylinder shell surface with a radius (11) and a center axis (10) which allow positioning of the joint adapter (2, 6, 7) against the stem module at different inclination angles around the center axis (10). The essentially radial arc shaped sections may also have an approximated arc shape like a polygon which may be a regular or irregular polygon. Preferably, the polygon has an extrusion like shape in a direction parallel to the center axis (10). Most preferably the contact points between the essentially radial arc shaped sections are located along the radius (11). Preferably the contact points may be axially offset to each other resulting in an anterior/posterior displacement. To enhance stability of the joint adapter preferably means are provided, which only allow modification of the inclination angle of the stem module (1) and the joint adapter (2, 6, 7) and block all or other degrees of freedom or movement like translation, and/or rotation under any angle different from said inclination angle. To secure the joint adapter (2, 6, 7) to the stem module (1) at least one bolt or screw (4) or other geometric means is provided. In general means for a form-locked join and/or a force-locked join are provided. There may also be means for sliding, preferably laterally sliding the joint adapter (2, 6, 7) into the stem module (1).

In a further embodiment the stem support surface (1c) and the adapter support surface (2d) have corresponding protrusions (2e) and/or recesses (1f), preferably interacting with each other, to prevent any movement like pivoting or sliding of the joint adapter (2, 6, 7) against the stem module (1). Preferably these protrusions (2e) and/or recesses (1f) prevent continuous movement in the inclination angle of the stem module (1) and the joint adapter (2, 6, 7), thus allowing positioning under varying inclination angles only in discrete steps. In general the surfaces may include a continuous, abbreviated, or interrupted undulating form or any surface coating or treatment increasing friction between the surfaces. The protrusions and recesses may be on both of the joint adapter (2, 6, 7) and the stem module (1). There may be at least one of a protrusion or a recess on one of the joint adapter (2, 6, 7) and the stem module (1).

According to a further embodiment, the radial arc shaped section (1c) of the stem module extends from or within a medial boundary (1d) to a lateral boundary (1e) of the most proximal aspect of the stem module (1). Alternatively the radial arc shaped section (1c) may only enclose a partial section between these boundaries.

In a further embodiment, at least one hole (1o, 1p) is provided in the stem module (1) to allow fastening the bolt or screw (4) in at least one of the holes to fix the joint adapter (2, 6, 7) at alternate positions relative to the stem module (1). The position depends on which hole is chosen for the bolt or screw (4). The holes may be threaded and/or may be displaced in anterior/posterior direction.

In a further embodiment, a single, continuous cavity (1g, 1h) is formed from the stem module (1) surface into the body of the stem module to hold the bolt or screw. In another embodiment such a cavity may be formed from the joint adapter (2, 6, 7) surface into the body of the joint adapter. The cavity may be displaced in anterior/posterior direction.

In another embodiment, the substantial portion of the cavity below the surface (1h) is greater in width from the opening (1g) at the surface. Preferably a ball screw is used for fastening the joint adapter (2, 6, 7) to the stem module (1) which has a threaded proximal section (4a), and distal spherical section (4b). This spherical section is to be inserted into and held in the cavity. Instead of the ball section of the screw, any equivalent means may be used, which allows sliding the screw and tightening it at various positions. Such an embodiment allows a continuous positioning of the stem module (1) and the joint adapter (2, 6, 7). This continuous positioning may be limited by any protrusions, recesses or undulations.

According to another embodiment, the joint adapter (2) has a plurality of holes (2x, 2y, 2z) for inserting a bolt or screw (4) dependent on the inclination angle or the relative position between the stem module (1) and the joint adapter (2, 6, 7). The holes may be threaded and/or may be displaced in anterior/posterior direction.

In a preferred embodiment, the joint adapter (2) is cup shaped and adapted to hold a liner (3). Such a liner may serve as the cup of a reverse joint. Preferably the liner (3) has a recessed spherical concavity (3a) which is located centrally originating from a surface (3b).

In an alternative embodiment, the joint adapter (2) is a trunion (6) which may either hold a spherical cap (8) or a liner (3) which has a recessed spherical concavity (3a). Preferably the trunion (6) has a substantially planar front surface (6a) opposing the adapter support surface (6d) which is intersected by a protrusion (6b) having a cavity (6c) located central to the protrusion which extends through the joint adapter.

The stem module (1), the joint adapter (2) and the bolt or screw (4) may be manufactured from titanium alloy, or other biocompatible metallic or non-metallic materials. The external surfaces of the device may be enhanced to allow by additive or subtractive processes, the application of texture or osteoinductive/osteoconductive material.

The liner (3) and the spherical cap (8) may be manufactured by using ultra high molecular weight polyethylene, or other biocompatible material suitable for use as a bearing surface in concert with a mating component of complimentary geometry.

The modular components may be offered in a variety of interchangeable sizes. The modular shoulder arthroplasty system of the present invention addresses osteoarthritis, trauma and/or cuff tear arthropathy. The invention is not limited to such applications and may be used to replace and/or treat any other joint.

The invention also provides a method of surgical reconstruction of a shoulder by inter alia: (i) providing a humeral prosthetic, comprising: a stem module (1) with a stem support surface (1c); and a joint adapter (2, 6, 7) adapted to hold either a liner (3) or a spherical cap (8), the joint adapter (2, 6, 7) having an adapter support surface (2d) which interfaces with the stem support surface (1c); wherein the stem support surface (1c) and the adapter support surface (2d) have corresponding approximately radial arc shaped sections which allow positioning of the joint adapter (2, 6, 7) against the stem module at different inclination angles between the longitudinal axis of the stem module (1) and the center axis of the joint adapter (2, 6, 7); (ii) positioning the joint adapter (2, 6, 7) against the stem module (1) at an inclination angle corresponding to the inclination angle of the humeral joint; (iii) securing the joint adapter to the stem module; and (iv) providing the humeral prosthetic within a patient's humerus and operatively connecting the humeral prosthetic to a patient's scapula.

These and other features and advantages of the present invention will become apparent from the following description of the invention that is provided in connection with the accompanying drawings and illustrated embodiments of the invention.

BRIEF DESCRIPTION OF THE DRAWINGS

FIG. 19 shows a stem module with a male post.

FIG. 20 shows a joint adapter mounted on a stem module with a male post.

DETAILED DESCRIPTION OF THE INVENTION

Figure 1:
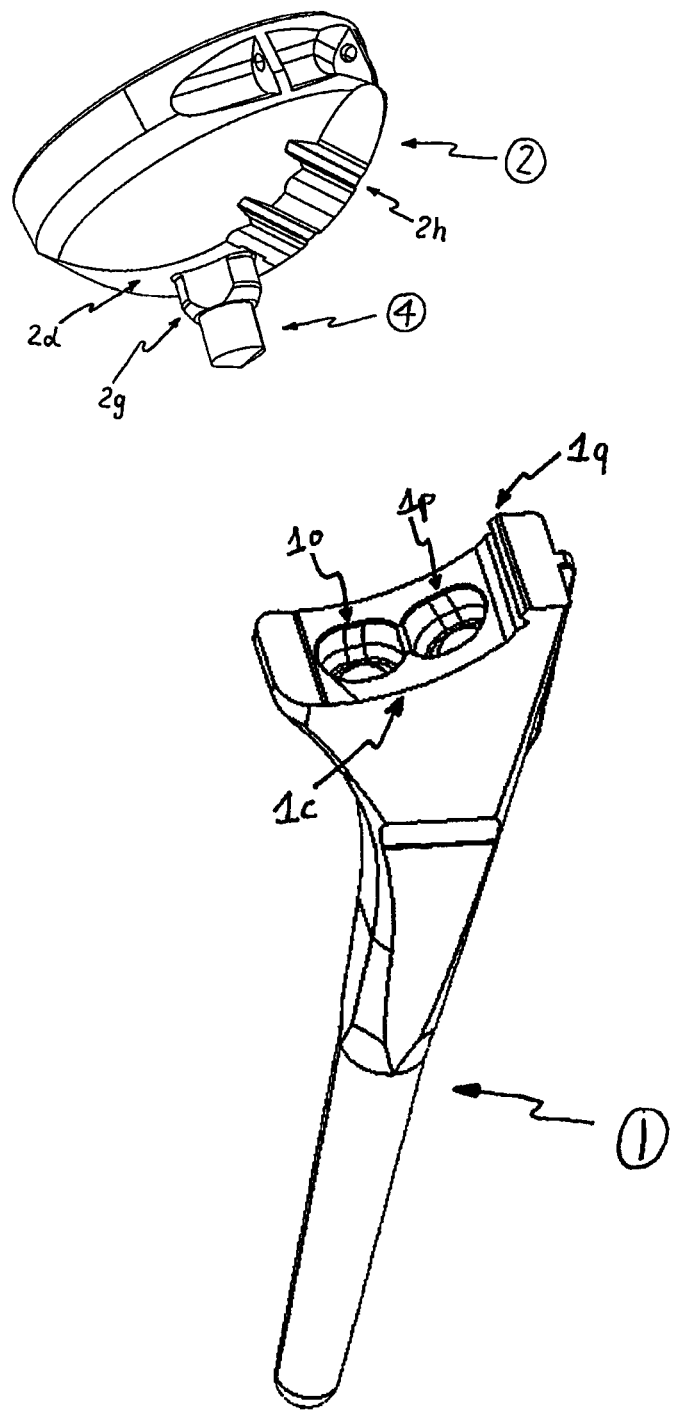
FIG. 1 shows a first embodiment of the humeral component of a shoulder prosthesis.

FIG. 1 shows a first embodiment of the humeral component of a shoulder prosthesis. It includes a stem module (1) and a joint adapter (2). The adapter support surface (2d) of joint adapter (2) interfaces with the stem support surface (1c) of stem module (1). Both have radial arc shaped sections. The radial arc shaped sections have sections of a cylinder surface and therefore only allow one kind of rotation around the cylinder axis. Rotation around other axis, specifically around axis perpendicular to the cylinder axis is not possible. The remaining degrees of freedom are rotation around a cylinder axis and there may be a translation parallel to the cylinder axis. A screw (4) through a preferably circular protrusion (2g) of the joint adapter (2) goes into one of the threaded holes (1o, 1p) defining alternate positions and therefore alternate inclination angles between the joint adapter (2) and the stem module (1). The screw (4) fixes the joint adapter to the stem module and locks the joint adapter against any rotation and/or translation. Recesses (1q) at the stem module (1) and protrusions (2h) at the joint adapter (2) preferably extend laterally to the arc shaped sections and interact with each other to prevent continuous movement of the stem module (1) against the joint adapter (2). They allow only positioning of the stem module (1) relative to the joint adapter (2, 6, 7) under discrete positions. There may be multiple joint adapters offered with the protrusion or the hole in different offset positions allowing the surgeon to choose whichever one gives him the desired anatomic outcome.

Figure 2:
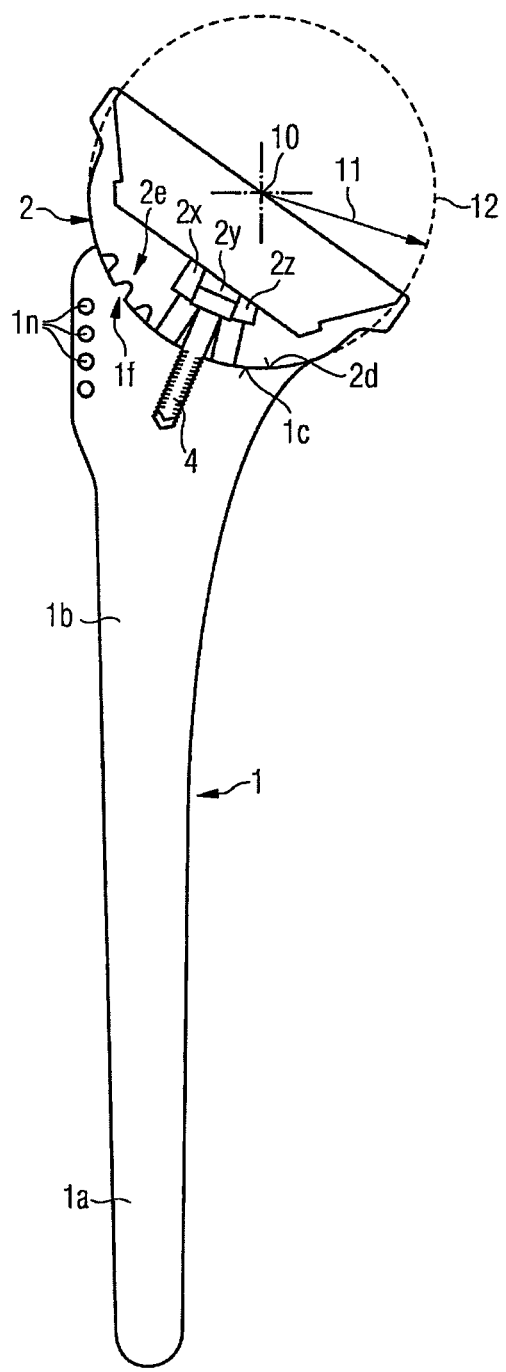
FIG. 2 shows a second embodiment of the humeral component of a shoulder prosthesis.

FIG. 2 shows a second embodiment of the humeral component of a shoulder prosthesis. It distinguishes over the first embodiment mainly by the different location of the holes for the screw (4). It includes a stem module (1) and a joint adapter (2). The stem module has a shank (1a, 1b) with an upper shank portion (1b). The upper shank portion bears a stem support surface (1c) to support a joint adapter. The joint adapter (2) is adapted to hold a liner in case of a reverse prosthesis or may be adapted to hold a spherical cap (8) for the use as a joint replacement. Furthermore the joint adapter (2) has an adapter support surface (2d) which interfaces with the stem support surface (1c). The stem support surface (1c) and the adapter support surface (2d) have corresponding radial arc shaped sections comprising segments of a cylinder shell surface (12) with a radius (11) and a center axis (10) which allow positioning of the joint adapter (2) against the stem module at different inclination angles around the center axis (10). The center axis (10) is shown here perpendicular to the plane of projection. The radial arc shaped sections are common with the other embodiments. A screw (4) is provided for fastening. This screw may be inserted through one of the holes (2x, 2y, 2z) dependent on the inclination of the joint adapter. There may be multiple joint adapters offered with the protrusion or the hole in different offset positions allowing the surgeon to choose whichever one gives him the desired anatomic outcomes.

Figure 3:
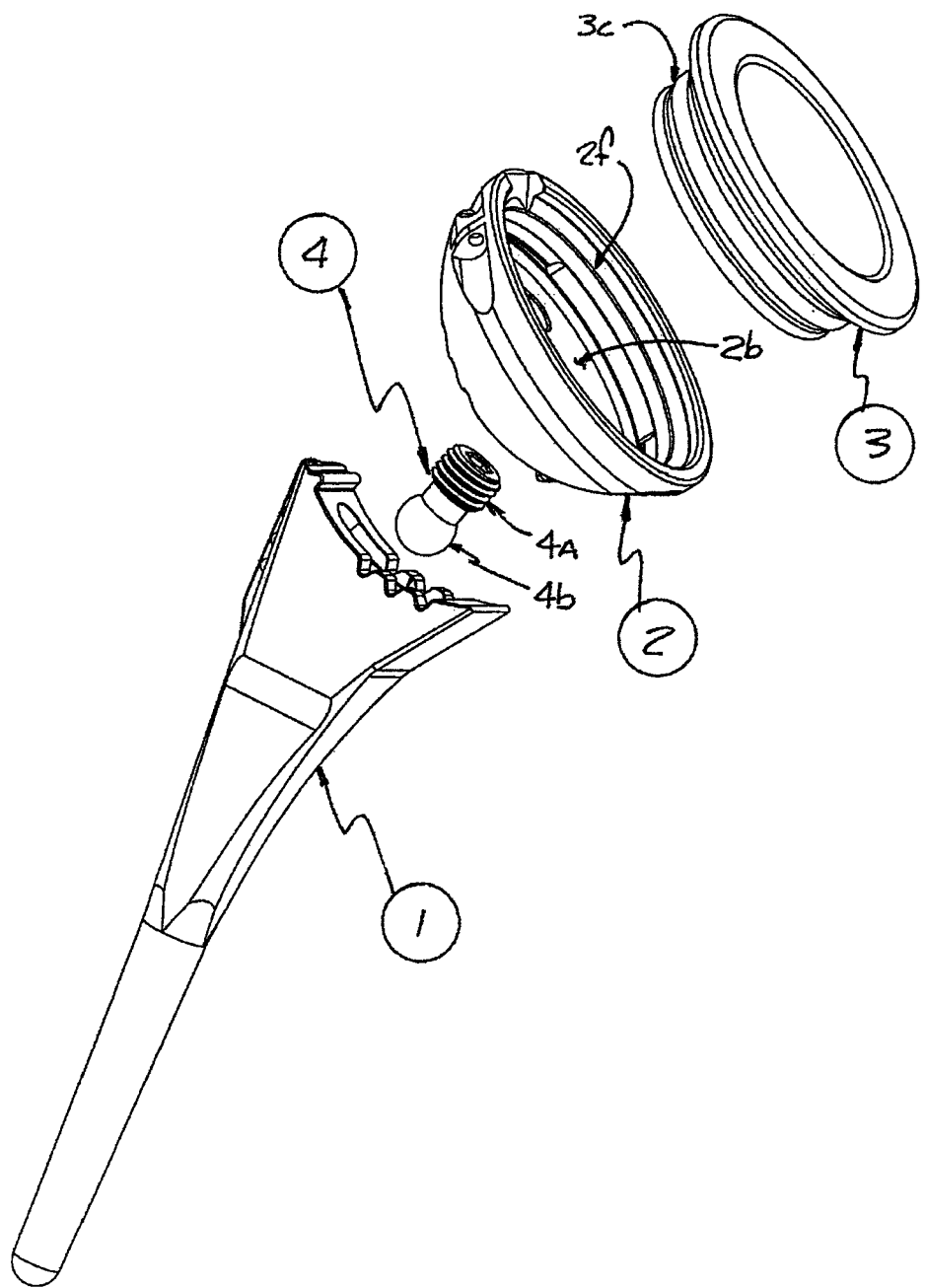
FIG. 3 shows a third embodiment of the humeral component of a shoulder prosthesis.

FIG. 3 shows a third embodiment of a humeral component (100c) of a shoulder prosthesis. It distinguishes over the first embodiment mainly by the different screw (4) and the way the screw is used to fix the components. It includes a stem module (1), a joint adapter (2) and a liner (3). Circumferential grooves concentric to the major body diameter are located on the outer surface (3c) of the liner (3) to interface with circumferential grooves concentric to the major body diameter on the surface (2f) of the joint adapter (2). A ball screw having a body used for fastening, featuring a threaded proximal section (4a), and distal spherical form (4b) is screwed into the rear surface (2b) of the joint adapter (2) and interfaces with the stem module (1).

In the above-identified embodiments, there may be multiple joint adapters offered with the protrusion or the hole in different offset positions, allowing medical personnel (e.g., the surgeon) to choose whichever one confers the desired anatomic outcome.

Figure 4A:
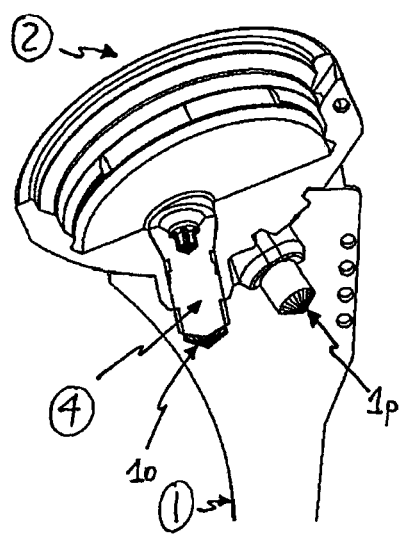
FIGS. 4a and 4b show a joint adapter according to the first embodiment mounted at different inclinations to the stem module.
Figure 4B:
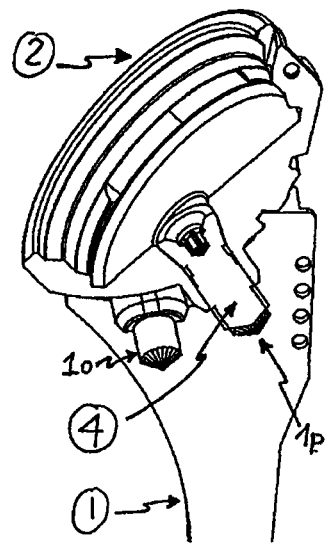

FIGS. 4a and 4b show a joint adapter (2) according to the first embodiment mounted at different inclination angles to the stem module (1), using the respective hole (1o, 1p) in the stem module (1) for the screw (4).

Figure 5A:
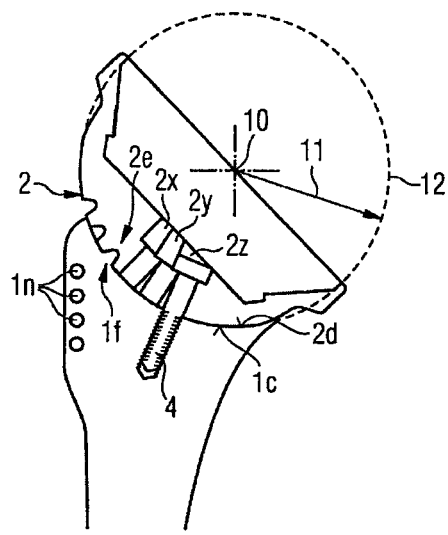
FIGS. 5a and 5b show a joint adapter according to the second embodiment mounted at different inclinations to the stem module.
Figure 5B:
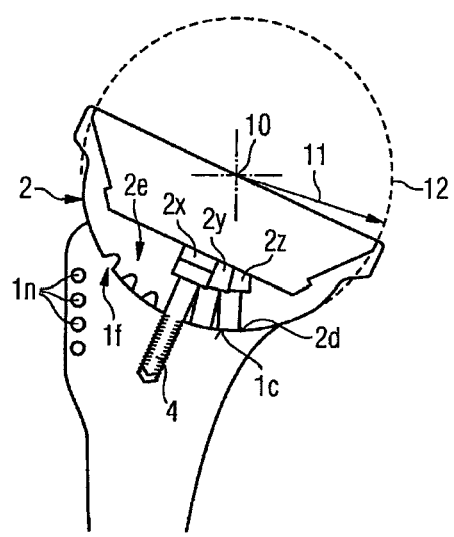

FIGS. 5a and 5b show a joint adapter (2) according to the second embodiment mounted at different inclination angles to the stem module (1), using the respective hole (2z, 2x) in the joint adapter (2) for the screw (4).

Figure 6:
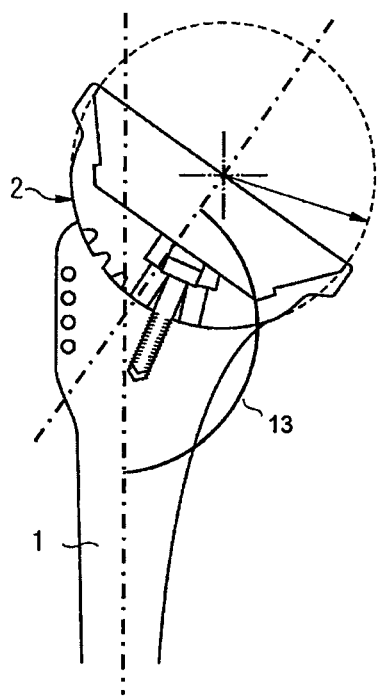
FIG. 6 shows the definition of the inclination angle.

FIG. 6 shows the definition of the inclination angle 13, also known as neck shaft angle. It is the angle between the longitudinal axis of the stem module (1), which is essentially the longitudinal axis of a bone (for example, humerus) into which the stem is inserted, and the center axis of the joint adapter (2, 6, 7). It may be in a range between 120 and 170 degrees and is preferably between 135 and 155 degrees. This inclination angle may be modified by positioning of the joint adapter (2, 6, 7) against the stem module (1).

Figure 7:
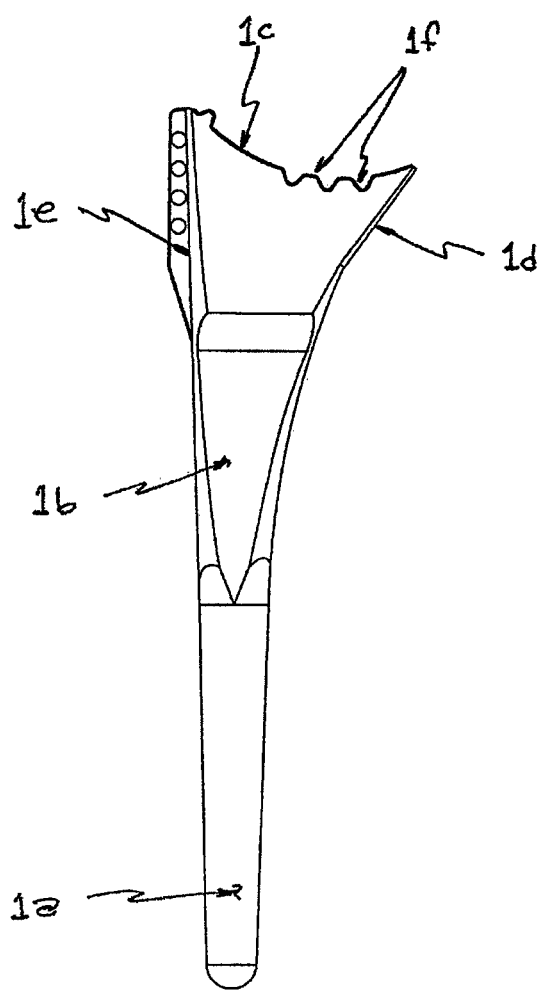
FIG. 7 shows a side view of a stem module in detail.

FIG. 7 shows a side view of the stem module in detail. The stem may either be a monobloc configuration or consist of several parts. It has a cylindrical or tapered distal aspect (1a) developing into a larger, polygonal form (1b). The most proximal aspect of the monobloc features the stem support surface (1c) as a radial arc extending from the medial boundary (1d) to the lateral boundary (1e) of the device. The stem support surface (1c) may include a continuous, abbreviated, or interrupted undulating form (1f).

Figure 8:
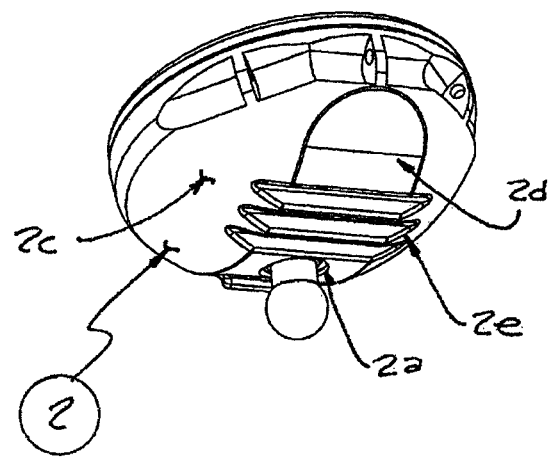
FIG. 8 shows a bottom view of a joint adapter.

FIG. 8 shows a bottom view of a joint adapter. It is a monobloc configuration presenting with a circular form when viewed en face. A single hole (2a) is located through the rear surface (2b). The reverse surface (2c) is generally spherical. The adapter support surface (2d) shaped as a radial arc intersects the reverse surface. The adapter support surface may include a continuous, abbreviated, or interrupted undulating form (2e).

Figure 9:
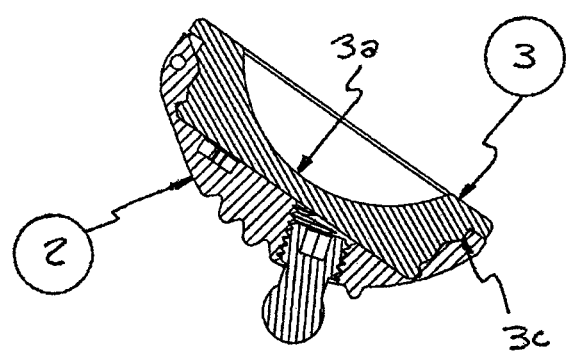
FIG. 9 shows a sectional view of a joint adapter.

FIG. 9 shows a sectional view of a joint adapter with inserted liner (3). The liner (3) is a monobloc configuration presenting with a circular form when viewed en face. A recessed spherical concavity (3a) is located centrally originating from inner surface (3b). Circumferential grooves concentric to the major body diameter on the outer surface (3c) interface with the joint adapter (2).

Figure 10:
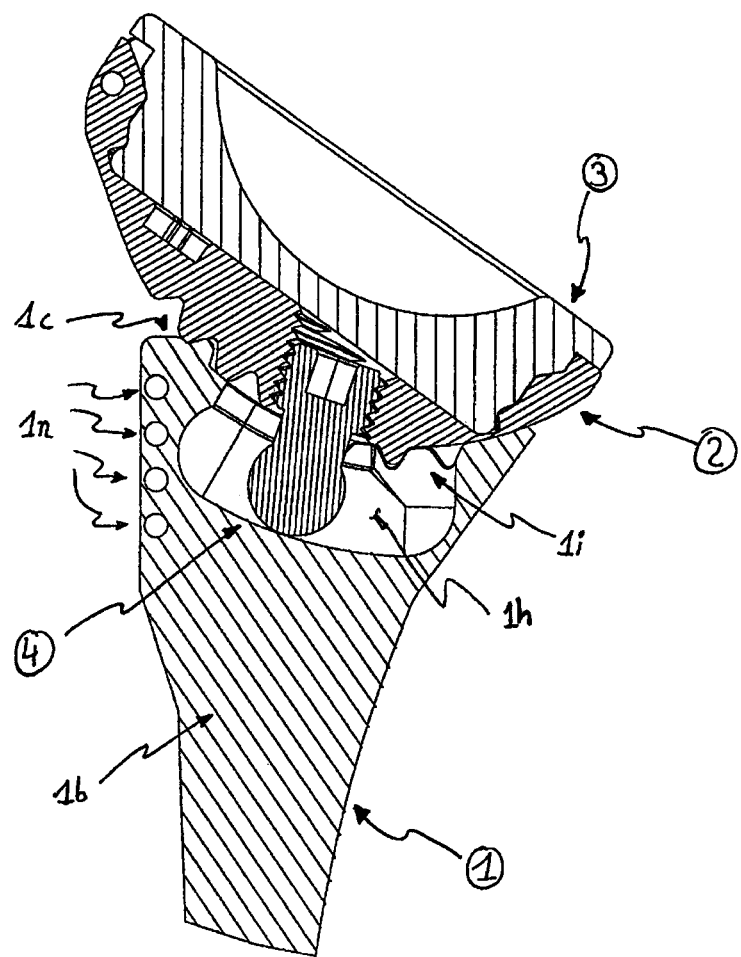
FIG. 10 shows a sectional view of a joint adapter mounted to a stem module.
Figure 11:
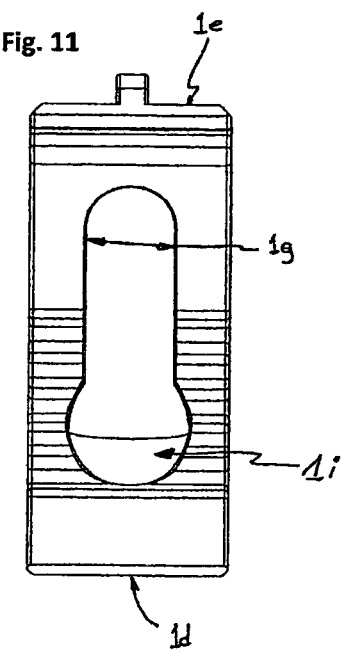
FIG. 11 shows a top view at the stem module.

FIG. 10 shows a sectional view of a joint adapter (2) mounted to a stem module (1). FIG. 11 shows a top view at the stem module (1). A single, continuous cavity (1h, 1i) is formed from the stem support surface (1c) into the body of the upper shank portion (1b). The substantial portion of the cavity below the surface (1h) may be greater in width from the opening (1g) at the surface. Holes (1n) are provided for fastening suture wires.

Figure 12:
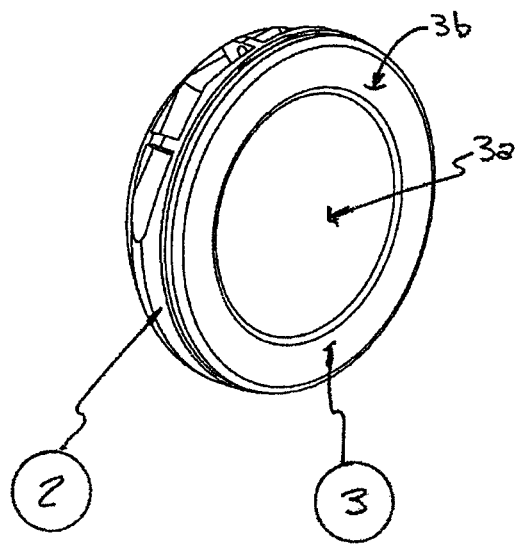
FIG. 12 shows a liner inserted into a joint adapter.

FIG. 12 shows a liner (3) inserted into a joint adapter (2). A recessed spherical concavity (3a) is located centrally originating from inner surface (3b).

Figure 13:
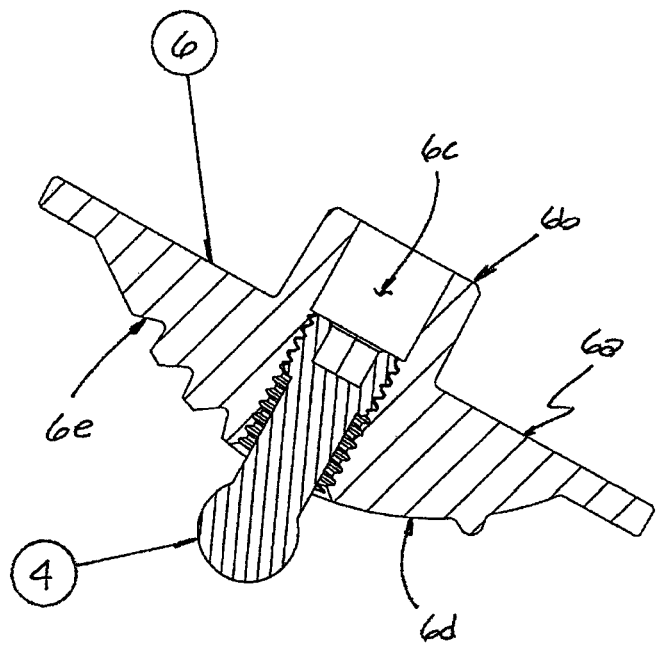
FIG. 13 shows a trunion as joint adapter.

FIG. 13 shows a trunion (6) as joint adapter. It has a monobloc body presenting as substantially circular when viewed enface. A substantially planar front surface (6a) is intersected by a protrusion (6b). A cavity (6c) is located central to the protrusion and extends through the boundaries of the body. The adapter support surface (6d) shaped as a radial arc intersects the reverse surface. The adapter support surface may include a continuous, abbreviated, or interrupted undulating form (6e).

Figure 14:
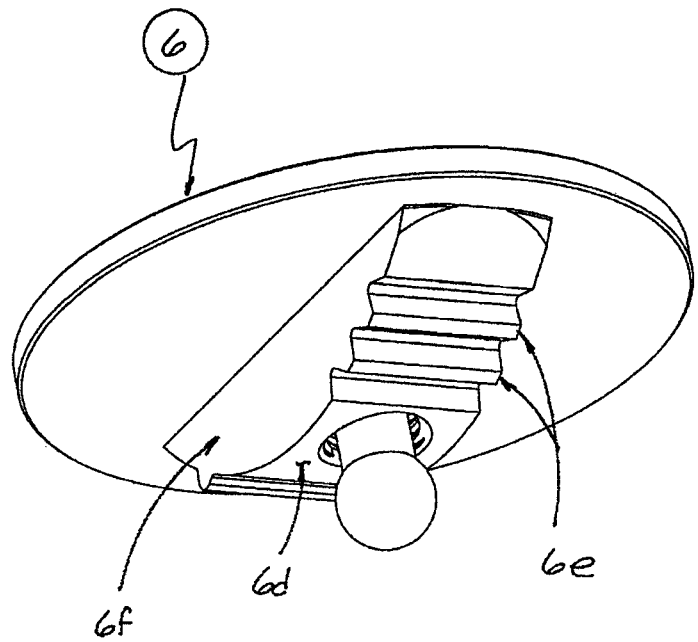
FIG. 14 shows a bottom view of a trunion.

FIG. 14 shows a bottom view of the trunion (6). The boundaries of the protrusion (6f) may be substantially planar. Such substantially planar boundaries may also be provided with any one of the joint adapters (2, 6, 7).

Figure 15:
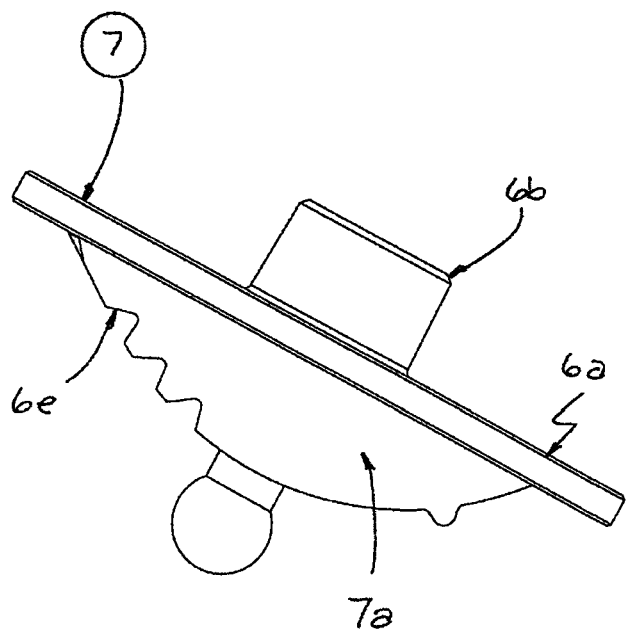
FIG. 15 shows a side view of a reverse trunion.

FIG. 15 shows a side view of a reverse trunion (7) as joint adapter. It has a monobloc body presenting as substantially circular when viewed en face. A substantially planar front surface (6a) is intersected by a protrusion (6b). A cavity may be located central to the protrusion and extends through the boundaries of the body. The adapter support surface shaped as a radial arc intersects the reverse surface and is part of a central spherical form (7a). The adapter support surface may include a continuous, abbreviated, or interrupted undulating form (6e).

Figure 16:
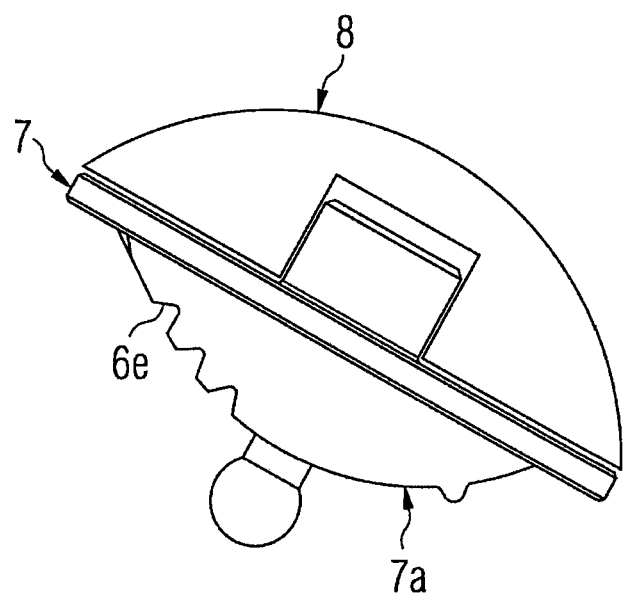
FIG. 16 shows a joint adapter with a spherical cap.

FIG. 16 shows a side view of a trunion (7) as joint adapter with a spherical cap (8).

Figure 17:
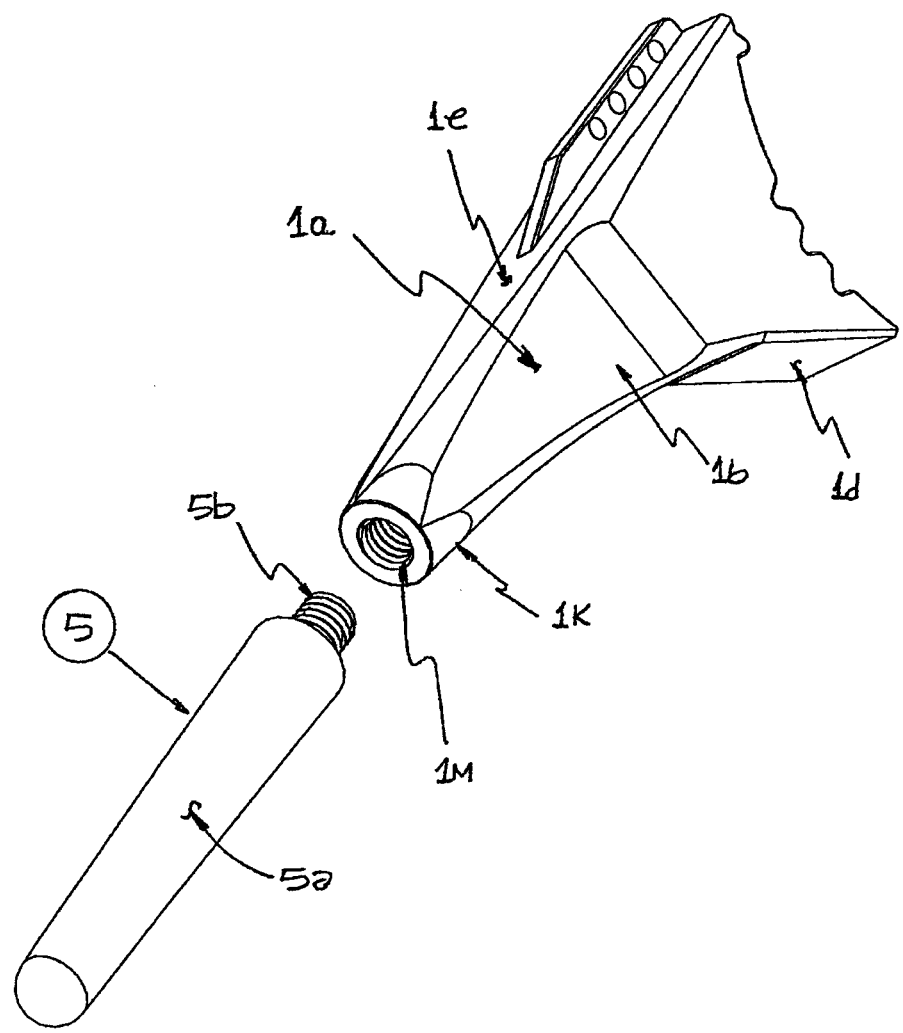
FIG. 17 shows a shank consisting of two parts.

FIG. 17 shows a stem module consisting of two parts. The stem module has a shank (1a) with a cylindrical distal aspect (1k) developing into a larger, polygonal form at the upper shank portion (1b). It has a medial boundary 1(d) and a lateral boundary (1e). A feature (1m) for the attachment of additional bodies like a distal shaft (5) is located at the most distal boundary of the device. The distal body may be cylindrical or tapered (5a). A proximal feature (5b) for the attachment to the stem module is located at the most distal boundary of the device.

Figure 18:
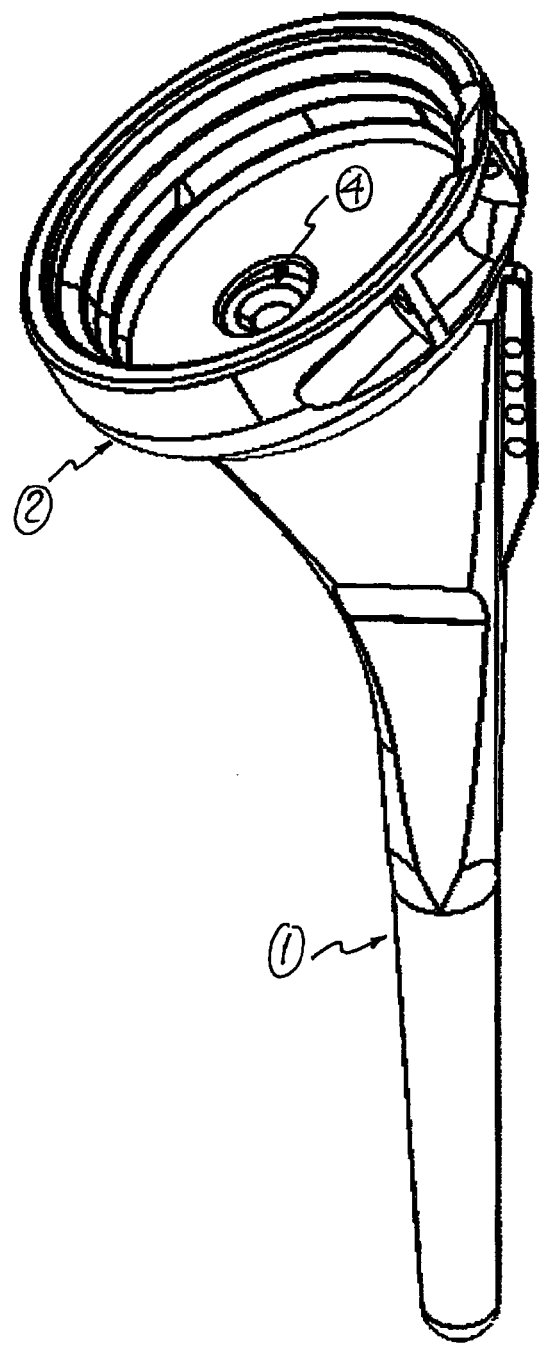
FIG. 18 shows a perspective view of an assembled humeral component of a shoulder prosthesis.

FIG. 18 shows a perspective view of an assembled humeral component of a shoulder prosthesis consisting of a stem module (1) and a joint adapter (2) fixed by a screw (4).

FIGS. 19-23(b) illustrate additional embodiments of a humeral component of a shoulder prosthesis of the present invention.

FIG. 19 shows a stem module (1) with a male post (4c) which fits into a slot in a joint adapter.

FIG. 20 shows a joint adapter (2) mounted on a stem module (1) with a male post (4c).

Figure 21:
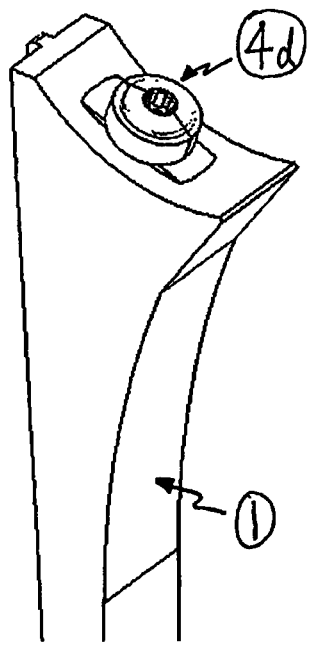
FIG. 21 shows a stem module with an expanding screw.

FIG. 21 shows a stem module (1) with an expanding screw (4d) which expands when tightened.

Figure 22A:
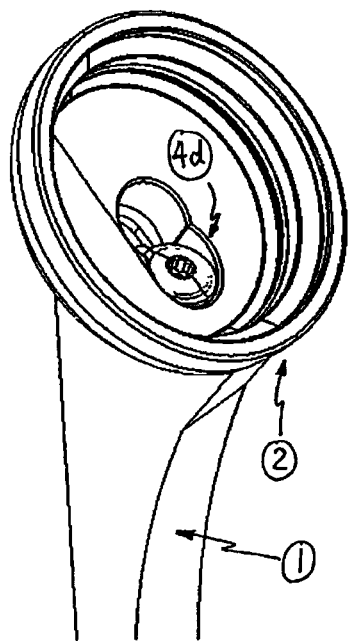
FIGS. 22a and 22b show a joint adapter mounted on a stem module with an expanding screw.
Figure 22B:
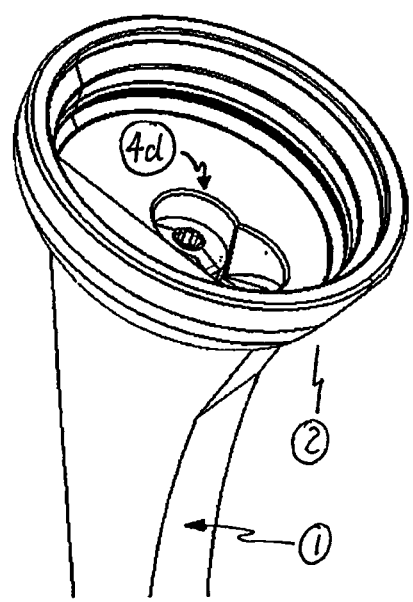

FIGS. 22a and 22b show a joint adapter (2) mounted on a stem module (1) with an expanding screw (4d). The screw fits into different holes of the joint adapter (2) according to the inclination angle.

Figure 23A:
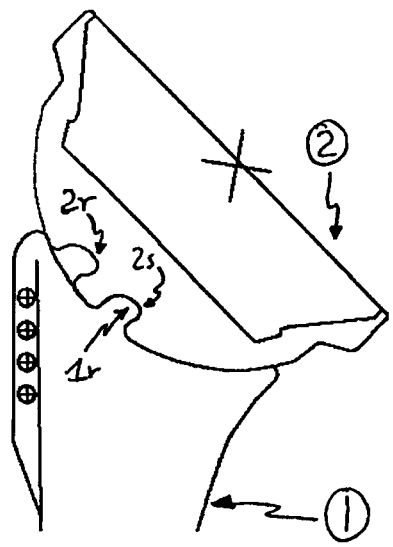
FIGS. 23a and 23b show a joint adapter mounted on a stem module with a key and slot connection.
Figure 23B:
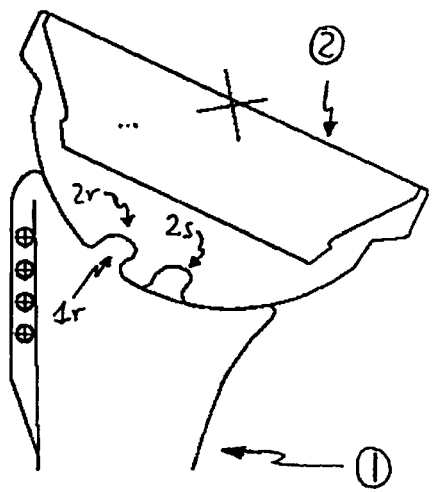

FIGS. 23a and 23b show a joint adapter (2) mounted on a stem module (1) with a key and slot connection. The key (1r) at the stem module (1) fits into one of the slots (2r, 2s) of the a joint adapter (2) depending on the inclination angle. The key and slots may be either on stem module (1), on the joint adapter (2) or on both. For assembly, the joint adapter (2) is inserted from the side into the stem module (1). This type of connection does not require a bolt or screw for primary fixation, although such a bolt or screw may be provided for additional securing/fixation.

Figure 24A:
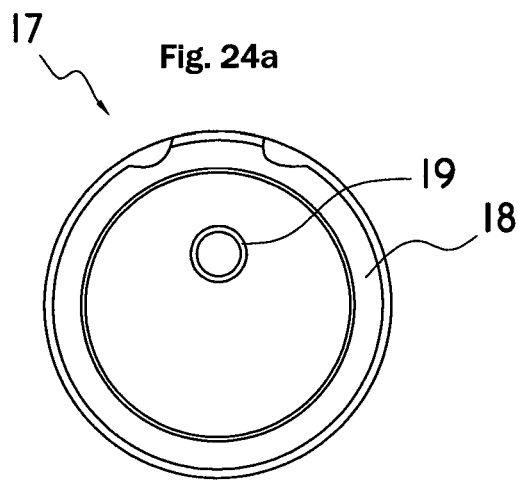
FIGS. 24a and 24b show a spacer and screw assembly of a shoulder prosthesis according to an embodiment of the invention.
Figure 24B:
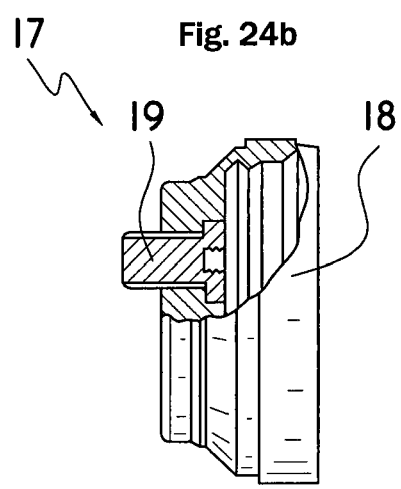
Figure 25A:
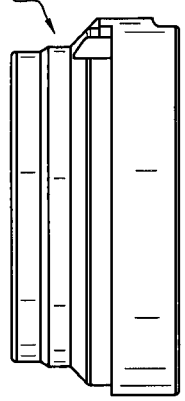
FIGS. 25a-25e show different views of the spacer of FIG. 24b.
Figure 25B:
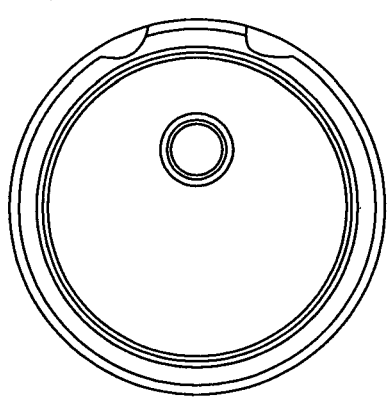
Figure 25C:
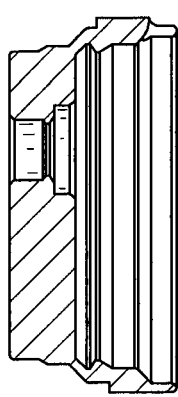
Figure 25D:
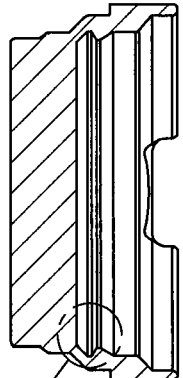
Figure 25E:
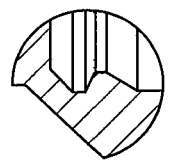
Figure 26A:
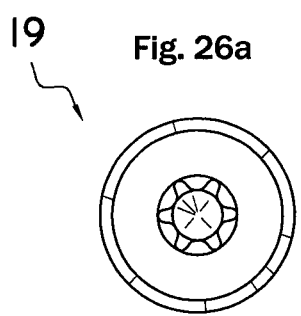
FIGS. 26a and 26b show different views of the screw of FIG. 24b.
Figure 26B:
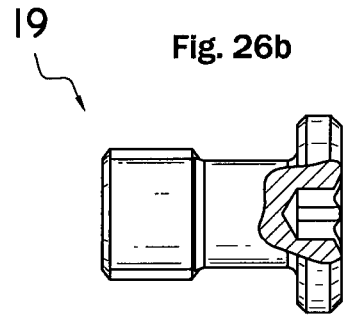

FIGS. 24a and 24b show a spacer and screw assembly (17) for use between the joint adapter (2) and the liner (3). FIGS. 25a-25e show different views of the spacer (18) of FIG. 24b. FIGS. 26a and 26b show different views of the screw (19) of FIG. 24b. The spacer may be formed of a metal or metal alloy, such as titanium or titanium alloy, or other biocompatible metallic or nonmetallic materials.

The humeral component (100a, 100b, 100c) of the prosthesis of the present invention may be employed in a total shoulder replacement procedure, for example, in a reverse (inverse) total shoulder replacement and/or in a primary shoulder replacement, due to the modular aspect of the prosthesis.

An exemplary method of assembling the modular shoulder reverse arthroplasty system of the present invention includes at least some of the following steps: inserting the ball screw (4) into cavity (2a) of the cup (2) and partially capturing the ball screw (4); inserting the distal spherical section (4b) into the cavity (1g) and positioning the ball screw (4) until surfaces (1c) and (2d) are collinear; further positioning the ball screw (4) to allow the integration of features 1f (FIGS. 7) and 2e (FIG. 8); selecting (by the user) the position of the cup (2) relative to the stem (1) with the plurality of locations determined by the number of undulations (1f and 2e) (in alternate embodiments, the plurality of undulations may be omitted); advancing the ball screw (4) until the assembly is secured; impacting the liner (3) into the cup (2).

An exemplary method of reverse shoulder arthroplasty (a total shoulder replacement procedure) may be conducted with the humeral component (100a, 100b, 100c) of the present invention, for example, with the humeral component 100a. The surgical proceeding (an exemplary delto pectoral approach) may include the following steps: patient positioning in the beach-chair position; exposure of the deltopectoral; release of the subscapularis; release of the glenohumeral capsule; humeral head resection; exposure of the glenoid.

The humeral preparation may include at least some of the following steps: employing a k-wire and a cannulated drill to open up a hole for IM reamer; fixing a cutting block assembly at a desired angle and positioning on the IM reamer; locating drill pins into the humeral head to secure the cutting block; removing the IM reamer and leaving the cutting block in position; resecting the humeral head using the cutting block to guide saw blade; removing the cutting guide and pins; inserting IM reamer and assembling a calcar cutting guide onto the IM reamer; inserting a calar drill cutter and drilling the cancellous calcar region; optionally, reaming the IM canal to depth mark until the desired size is achieved; connecting different size rasps to rasp the canal until the desired size is achieved; employing different reamers to ream the canal; connecting the cup (with the specific angle, diameter and offset) to the rasp; connecting the liner and optionally the spacer to the cup; assembling the stem and the cup (based on trial sizes and angles) and implanting into humerus; optionally checking tension; assembling definite liners (and spacers if required).

The glenoid preparation may include at least some of the following steps: advance a drill guide over a k-wire on the center of the glenoid; drill a pilot hole through the drill guide; remove the drill guide; advance a primary cannulated central reamer over the previously-positioned k-wire; conduct reaming until the depth stop; remove the primary central reamer leaving the k-wire in position; advance a cannulated reamer over the k-wire; conduct reaming until depth stop; optionally employ a correction reamer to ensure entire reaming of the bone circumference; attach a metal back to an impactor; impact the metal back; insert drill guide in bushing and drill k-wire to a pre-determined depth; insert superior, inferior and central screws; centralize a coring reamer over the metal back and ream to depth; assemble a glenoid head (glenosphere) into the metal back central hole; ensure position is correct and all fenestrations are aligned with the metal back; impact the glenoid head until it is seated.

The reverse shoulder system of the present invention reverses the normal biomechanics between the scapular and humeral components. Compared to anatomic systems, the center of rotation is positioned medially and inferiorly, to shorten the deltoid lever and arm and reduce the deltoid tension. This allows the muscles of the deltoid group to compensate for rotator cuff deficiency. The stem may be either cemented or not cemented (with a CaP coating, for example). The glenoid component is fixated with screws (for example, three screws) and may be coated (for example, CaP coated) for secondary fixation.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A humeral component of a shoulder prosthesis comprising:
- a stem module comprising a shank and an upper shank portion with a stem support surface, and
- a joint adapter adapted to hold either a liner or a spherical cap, the joint adapter having an adapter support surface which interfaces with the stem support surface, the joint adapter having a plurality of holes for inserting a fastening device dependent on an inclination angle corresponding to the inclination angle of a patient's humeral joint;
- wherein the stem support surface and the adapter support surface have corresponding approximately radial arc shaped sections which comprise segments of a cylinder shell surface with a radius and a center axis for positioning of the joint adapter against the stem module at different inclination angles between the longitudinal axis of the stem module and the center axis of the joint adapter; and
- wherein the joint adapter is fastened to the stem module.

2. The humeral component of a shoulder prosthesis according to claim 1, wherein the stem support surface and the adapter support surface have corresponding protrusions and recesses to prevent pivoting of the joint adapter against the stem module.

3. The humeral component of a shoulder prosthesis according to claim 1, wherein the radial arc shaped section of the stem module extends from, or within, a medial boundary to a lateral boundary of the most proximal aspect of the stem module.

4. The humeral component of a shoulder prosthesis according to claim 1, wherein at least one hole is provided in the stem module to allow fastening of a bolt or screw in the at least one hole to fix the joint adapter at alternate positions relative to the stem module.

5. The humeral component of a shoulder prosthesis according to claim 1, wherein a single, continuous cavity is formed from the stem module surface into the body of the stem module to hold the bolt or screw.

6. The humeral component of a shoulder prosthesis according to claim 5, wherein the substantial portion of the cavity below the surface is greater in width from the opening at the surface.

7. The humeral component of a shoulder prosthesis according to claim 1, wherein a ball screw is used for fastening the joint adapter to the stem module which has a threaded proximal section, and distal spherical section.

8. The humeral component of a shoulder prosthesis according to claim 1, wherein fastening device inserted into the plurality of holes of the joint adapter comprises a bolt or screw.

9. The humeral component of a shoulder prosthesis according to claim 1, wherein the joint adapter is cup shaped and adapted to hold a liner.

10. The humeral component of a shoulder prosthesis according to claim 9, wherein the liner has a recessed spherical concavity which is located centrally originating from a surface.

11. The humeral component of a shoulder prosthesis according to claim 1, wherein the joint adapter is a trunion to hold a spherical cap.

12. The humeral component of a shoulder prosthesis according to claim 11, wherein the trunion has a substantially planar front surface opposing the adapter support surface which is intersected by a protrusion having a cavity located central to the protrusion which extends through the joint adapter.

* * * * *